US012763174B2

(12) United States Patent
Kazeev et al.

(10) Patent No.: US 12,763,174 B2
(45) Date of Patent: Oct. 13, 2026

(54) SPARSE REPRESENTATION FOR MACHINE LEARNING THE PROPERTIES OF DEFECTS IN 2D MATERIALS

(71) Applicants: Constructor Technology AG, Schaffhausen (CH); Constructor Education and Research Genossenschaft, Schaffhausen (CH)

(72) Inventors: Nikita Kazeev, Singapore (SG); Andrey Ustyuzhanin, Ferney Voltaire (FR); Abdalaziz Rashid Al-Maeeni, Moscow (RU); Maxim Faleev, Barcelona (ES); Ruslan Lukin, Kazan (RU); Alexander Tormasov, Bremen (DE); Ignat Romanov, Beijing (CN); Serg Bell, Singapore (SG); Stanislav Protasov, Singapore (SG); Nikolay Dobrovolskiy, Alanya (TR)

(73) Assignees: Constructor Technology AG, Schaffhausen (CH); Constructor Education and Research Genossenschaft, Schafffausen (CH)

( * ) Notice: Subject to any disclaimer, the term of this patent is extended or adjusted under 35 U.S.C. 154(b) by 569 days.

(21) Appl. No.: 18/307,628

(22) Filed: Apr. 26, 2023

(65) Prior Publication Data

US 2024/0363204 A1 Oct. 31, 2024

(51) Int. Cl.

| | |
|---|---|
| ***G16C 60/00*** | (2019.01) |
| ***G16C 20/30*** | (2019.01) |
| ***G16C 20/70*** | (2019.01) |

(52) U.S. Cl.

CPC ............. *G16C 60/00* (2019.02); *G16C 20/30* (2019.02); *G16C 20/70* (2019.02)

(58) Field of Classification Search

CPC ......... G16C 60/00; G16C 20/30; G16C 20/70

See application file for complete search history.

(56) References Cited

PUBLICATIONS

Huang et al. (Unveiling the complex structure-property correlation of defects in 2D materials based on high throughput datasets. npj 2D Mater Appl 7, Apr. 6, 2018). https://doi.org/10.1038/s41699-023-00369-1) (Year: 2018).*

(Continued)

*Primary Examiner* — Christian T Bryant

(74) *Attorney, Agent, or Firm* — ESPE Legal Consultancy FZ-LLC

(57) ABSTRACT

A method for predicting at least one property of a crystal of a material, with the crystal exhibiting at least one point defect. At least one module samples structures of materials and point defects of the crystal. The method comprises: providing a neural network. The neural network comprises: receiving as input a structure of the material and an ideal crystal unit cell structure. The neural network also comprises: outputting at least one target quantity and using a generated set of data and representing the point defect. The point defect represents a set of coordinates and a type of the point defect and a crystal unit cell structure. The neural network further comprises: receiving as input at least one of a cloud of defect points and a global state vector. The neural network additionally comprises outputting a vector.

20 Claims, 7 Drawing Sheets

(56) References Cited

PUBLICATIONS

Kazeev et al. (Sparse representation for machine learning the properties of defects in 2D materials. npj Comput Mater 9, 113 (2023). https://doi.org/10.1038/s41524-023-01062-z) (Year: 2023).*
Xie et al. (Crystal graph convolutional neural networks for an accurate and interpretable prediction of material properties. Phys. Rev. Lett. 120, 145301 (2018)) (Year: 2018).*
Chen et al. (Graph networks as a universal machine learning framework for molecules and crystals. Chem. Mater. 31, 3564â3572 (2019)) (Year: 2019).*
Tarak K. Patra, et al. Defect Dynamics in 2-D MoS2 Probed by Using Machine Learning, Atomistic Simulations, and High-Resolution Microscopy, Defect Dynamics in 2-D MoS2 Probed by Using Machine Learning, Atomistic Simulations, and High-Resolution Microscopy.pdf.
Nathan C. Frey, et al. Machine Learning-Enabled Design of Point Defects in 2D Materials for Quantum and Neuromorphic Information Processing, Machine Learning-Enabled Design of Point Defects in 2D Materials for Quantum and Neuromorphic Information Processing.pdf.
Shreeja Das, et al. 19—Machine learning in materials modeling—fundamentals and the opportunities in 2D materials, 2020, Machine learning in materials modeling-fundamentals and the opportunities in 2D materials—ScienceDirect.pdf.
Olexandr Isayev, et al. Universal fragment descriptors for predicting properties of inorganic crystals, Jun. 5, 2017, Universal fragment descriptors for predicting properties of inorganic crystals.pdf.
Suvo Banik, et al. Learning with Delayed Rewards—A case study on inverse defect design in 2D materials, Jun. 19, 2021, Learning with Delayed Rewards—A case study on inverse defect design in 2D materials.pdf.
George Alexandru Nemnes, et al. Feature selection procedures for combined density functional theory—artificial neural network schemes, Apr. 12, 2021, Feature selection procedures for combined density functional theory—artificial neural network schemes.pdf.
Anus Manzoor, et al. Machine Learning Based Methodology to Predict Point Defect Energies in Multi-Principal Element Alloys, Jun. 1, 2021, Machine Learning Based Methodology to Predict Point Defect Energies in Multi-Principal Element Alloys.pdf.

* cited by examiner

SPARSE REPRESENTATION FOR MACHINE LEARNING THE PROPERTIES OF DEFECTS IN 2D MATERIALS

TECHNICAL FIELD

Embodiments relate generally to predicting properties of a material. More particularly, embodiments relate to predicting properties of a crystal.

BACKGROUND

In general, models and/or systems do not apply to crystals with defects. Further, state-of-the-art algorithms usually underperform on crystal structures with defects. The neighbourhoods of most atoms are not affected by point defects. State-of-the-art machine learning algorithms struggle to accurately learn the properties of a crystal with defects.

The article "Machine Learning-Enabled Design of Point Defects in 2D Materials for Quantum and Neuromorphic Information Processing" (Nathan C. Frey, Deji Akinwande, Deep Jariwala, and Vivek B. Shenoy: ACS Nano 2020, 14, 10, 13406-13417, Sep. 8, 2020) discloses an approach based on deep transfer learning, machine learning, and first-principles calculations to rapidly predict key properties of point defects in 2D materials using physics-informed featurization to generate a minimal description of defect structures and present a general picture of defects across materials systems.

The article "Defect Dynamics in 2-D MoS2 Probed by Using Machine Learning, Atomistic Simulations, and High-Resolution Microscopy" (Tarak K. Patra, Fu Zhang, Daniel S. Schulman, Henry Chan, Mathew J. Cherukara, Mauricio Terrones, Saptarshi Das*, Badri Narayanan*, and Subramanian K. R. S. Sankaranarayanan: ACS Nano 2018, 12, 8, 8006-8016 Aug. 3, 2018) discloses a combination of genetic algorithms (GA) with MD to investigate the extended structure of point defects, their dynamical evolution, and their role in inducing the phase transition between the semiconducting (2H) and metallic (IT) phase in monolayer MoS2.

SUMMARY

Embodiments described herein provide a method for predicting properties of a material having defects.

Further, embodiments described herein offer a way for machine learning systems to precisely predict nonlinear quantum mechanics behaviour of defects.

BRIEF DESCRIPTION OF THE DRAWINGS

Subject matter hereof may be more completely understood in consideration of the following detailed description of various embodiments in connection with the accompanying figures, in which.

Figure 1A:
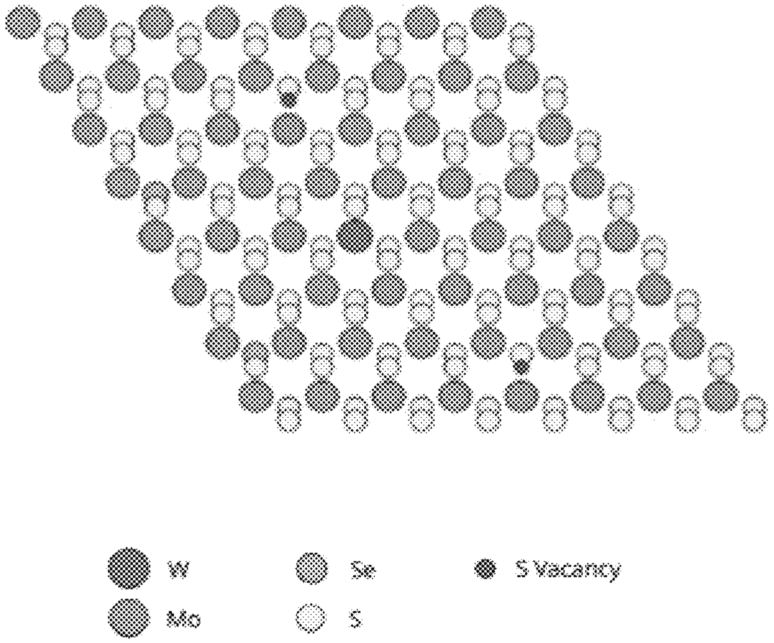
FIG. 1*a* to FIG. 1*d* are block diagrams of a transition from a full representation (FIG. 1*a*) to a sparse representation (FIG. 1*d*) using the example of a MoS2 supercell, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The object is solved by a method for predicting at least one property of a crystal of a 2D material showing at least one point having a defect (point defect).

Structures of the 2D material and point defects are sampled by a module. A neural network (predicting module) is provided to receive as input a structure of the 2D material and an ideal crystal unit cell structure and to output at least one target quantity. The structure of the material can be sparse for optimization purposes. The meaning of "sparse" is explained in more detail below.

The neural network uses a generated set of data. The point defect is represented as a set of coordinates and a type of the point defect, and a crystal unit cell structure.

For convenience the point defect representation can be combined into a tuple, with the tuple comprising a first component and a second component. The first component comprises a set of coordinates and a type of the point defect. The second component comprises a crystal unit cell structure, represented as a 3D vector. By way of example, the size of the cell structure may vary from 0.01 to 0.10 mm in size. However, it goes without saying that the cell structure of the material may also be of a different size.

In embodiments, at least one of a cloud of defect points (point cloud of defects) and a global state vector is received by the method as input, wherein the method outputs a vector.

The object is further solved by a module for sampling structures of 2D materials and point defects. Sampling can be performed by using at least one of the following: An ab initio method on HPC and/or an open data basis.

Two-Dimensional Material (2D-Material)

In an embodiment, nanomaterials are classified by the total number of their nanoscopic dimensions. In case all three dimensions of a material are nano-sized, it would be referred to as a OD (zero-dimensional) material, also referred to as a nanoparticle. Should two dimensions of a material be nano-sized, with one other dimension by far larger than the other dimension, then the material is referred to as a 1D material or a nanotube/nanowire. Should only one dimension be nano-sized, the material would be referred to as a 2D material. (Example: A large but very thin sheet of paper).

Despite the following, embodiments refer to a 2D material, embodiments can also be used to predict specific properties of 3D materials with defects.

In materials science the term single-layer materials or 2D materials refers to crystal solids. So-called solid crystals commonly include a single layer of atoms. In other embodiments, solid crystals can include several layers of atoms. A typical number of layers is less than 5. The materials and layers described herein are by way of example only. Rather, embodiments can be utilized for a single layer of atoms, and/or several layers of atoms included in 2D and 3D materials.

2D materials may have various desired quantum emissions. Exemplary, but not exclusively, two-dimensional materials show electronic and optoelectronic properties, properties to be used in solid-state devices. The 2D materials may be one or more unit layers of MoS2, WSe2, h-BN, GaSe, InSe, and black phosphorous (BP).

Point Defects

The introduction of a defect site into a lattice creates unsaturated defect states. A so-called wave function of a defect site fluctuates over a distance of a few unit-cell constants. The fluctuation depends on the localization of the electrons in the host lattice. This fact results in so called localized defect levels in the energy spectrum of the solid.

By way of example, the fluctuation may lead to localized features in the energy spectrum of the whole material.

According to quantum embedding theories, the defect levels are governed by the wave function overlap. The defect levels may be dominated by the exchange integral of the unsaturated electrons in the background of the valence band electrons. The properties of a defect complex composed of more than one defect sites are governed by the interference of wave functions of the defect sites, respectively.

It follows that the formation energy, positions of defect energy levels, and a so-called HOMO-LUMO gap are a nonlinear function of defect configurations. The size of the HOMO-LUMO gap can be used to predict both the strength and the stability of transition metal complexes.

As described in more detail further below, an embodiment can evaluate a descriptor-based approach for the collected data.

Controllable Defect Engineering

Generally speaking, the controllable defect engineering is introduced to control the growth defect.

By the term controllable defect engineering, embodiments understand the introduction of vacancies and/or desired impurities.

Hereinafter, embodiments understand the term controllable defect engineering in the context of a crystal structure.

The following crystallographic defects are known: Crystallography is the name for the field that deals with the study of crystal structures.

According to an embodiment, the point defect comprises at least one of the following: A vacancy defect, where an atom is missing from a crystal lattice and/or a substitution defect, where an atom is replaced with a different atom and/or an interstitial defect, where an atom occupies a position in the crystal structure which is usually empty.

In the following, the different defects are discussed in detail.

Vacancy defect: A lattice site which is supposed to be occupied in a perfect crystal is vacant.

Interstitial defect: Atoms occupy a site in the crystal structure in a position which usually is not occupied by an atom.

Frenkel defect: A nearby pair of a vacancy and an interstitial may be referred to as Frenkel defect. The Frenkel defect is caused when an ion moves into an interstitial site and creates a new vacancy.

Substitutional defect: An irregular (additional) atom may be incorporated at a regular atomic site in the crystal structure. The irregular atom is not positioned at a vacant (interstitial) site (referred to above as interstitial defect). The atom is not supposed to be anywhere in the crystal. Thus, the irregular atom is referred to as an impurity.

Antisite defect: An antisite defect occurs in a compound when atoms of different types exchange positions.

Topological defect: A topological defect refers to a region in a crystal where the normal chemical bonding environment is topologically different from the surroundings.

It goes without saying that other defects may also be present.

The controllable defect engineering enables property changes and new functionalities in the crystal material.

According to an embodiment the property comprises at least one of the following: A potential energy and/or a Fermi level and/or an electron band structure and/or a phonon structure and/or a colour. The Fermi Level is an energy level which is occupied by an electron orbital at temperature equals of 8 Kelvin.

A phonon is a collective excitation in a periodic, elastic arrangement of atoms or molecules in a condensed matter.

The crystallographic defect is an interruption of the regular patterns of arrangement of atoms or molecules in crystal solids. The positions and orientations of particles, which are repeating at fixed distances determined by the unit cell parameters in crystals, exhibit a periodic crystal structure.

According to another embodiment the crystal unit cell structure is represented as a vector.

The reduced dimensionality in layered two-dimensional materials makes it possible to manipulate defects atom by atom.

It allows to tune the properties of the crystal to the limits of quantum mechanics limits. Embodiments can be commercialised in products of the semiconductor industry in the post-Moore era. It may also find its way into new technologies such as quantum computers, catalysts and photovoltaics.

Machine Learning

Machine learning is an application of artificial intelligence. Machine learning systems installed in a computer, provide the ability to automatically learn and improve data stored in a database from experience without being explicitly programmed.

Machine learning is about developing computer programs that accesses and uses data to learn on their own.

Latest developments in the field of high volume material databases have greatly improved the application of deep learning methods in atomistic predictions.

By way of example, machine learning systems trained on so called density functional theory calculations may be used e.g. to identify materials for batteries and catalysts. It goes without saying that there is a variety of other application fields.

Through the use of machine learning systems, the design of new materials may be accelerated. Thus, material properties may be predicted with an improved accuracy. Computational costs may be reduced to a considerable extent.

Deep learning is a part of a further system, containing machine learning systems based on so called artificial neural networks with representation learning. Deep learning can be provided on a supervised scale or on a semi-supervised scale or on an unsupervised scale.

A variety of fast and accurate deep learning methods have been developed.

The following procedures are examples of graph neural networks (GNN), such as MEGNet, CGCNN, SchNet, GemNet.

A machine learning system comprises at least one parameter, values of which are obtained by training the machine learning model. The parameter is stored and the model used for computing predictions. Machine learning systems are proposed for predicting formation energies of single point defects across different materials. Machine learning may be employed to predict the energetic and electronic properties of defects. The accuracy to predict the energetic and electronic properties of defects by means of machine learning may be demonstrated in a statistical way. The ability of these systems in reproducing a quantum oscillation behaviours of defect properties may be demonstrated as a function of defect configuration.

Graph Neural Networks (GNN)

GNN Architectures for Materials

In an embodiment, a GNN architectures can be utilized for materials. Machine learning offers at least two principal approaches to predict atomistic properties.

The first approach is referred to as graph neural networks (GNN). The second principal is referred to as physics-based descriptors.

The physics-based descriptor is referred to in detail below.

Graph neural networks (GNN) are uniquely suitable for modelling atomic systems. In an embodiment, graph neural networks provide an invariance to permutations and/or an invariance to both rotations and translation. Graph neural networks also provide natural encoding of the locality of interactions.

In an embodiment, graph neural networks (GNNs) outperform physics-based descriptors.

By way of example, embodiments hereinafter refer to graph neural networks (GNNs). In the following, graph neural networks are referred to as GNN.

State of the art systems propose applying a convolutional GNN to any kind of materials.

By way of example, GNN incorporates a Voronoi-tessellated atomic structure. Besides a 3-body correlation of neighbouring atoms the GNN further incorporates chemical representation of interatomic bonds.

Also, a GNN architecture performs message passing on both the interatomic bond graph and its line graph corresponding to bond angles.

Another system provides a hybrid model between transformers and GNNs. The system allows for more expressive aggregation operations.

In an embodiment, models and/or systems are capable of handling any atomistic Structures.

GNN—Message Passing Neural Network

Many types of graph neural networks (GNN) can be utilized.

The message passing neural network has been introduced for analyzing material structures. To prepare a training sample, a graph is constructed out of a crystal configuration. In order to do so, atoms are referred to as graph nodes. Graph edges connect nodes at distances that are smaller than a predefined threshold. Periodic boundary conditions are used to establish the connection: To achieve a significantly large threshold, an edge may connect a node to its image in an adjacent supercell. Specific property vectors are used to determine nodes and edges. The node comprises the atomic number. Wherein the edge comprises the Euclidean distance between the atoms that are connected by the edge.

A layer of a message-passing neural network transforms a graph into another graph showing the same connectivity structure. To perform the transformation of the graph, only the nodes, edges, and global attributes are changed. The layers are arranged one on top of the other to form a stack. The stack of layers provides an expressively deep architecture.

The following assumptions apply:

G=(V, E, u) is a crystal graph from the previous operation.

Vectors $V=\{v_i\}|V|i=0$ represent the nodes.

Wherein: $v_i \in Rdv|V|$ represents the number of atoms in the supercell.

In the example, the edge states are represented by vectors $\{e\}|E|k=0$.

Wherein $e_k \in Rde$.

Each edge comprises at least one of the following:

a sender node $v^s \in \{0, \ldots, |V|-1\}$, a receiver node $v^r \in \{0, \ldots, |V|-1\}$, and a vector of edge attributes.

An edge $(v^s_k, v^r_k, e_k)$ represents a tuple.

Wherein the superscripts s, r denote the sender and the receiver nodes, respectively.

Additional assumptions are formulated as follows:

A global state vector $u \in Rde$ represents the global state of the system.

Input Graph:

In an input graph, the global state is used to provide the algorithm with information about the system as a whole. In the case of the sparse representation, the information represents the composition of the base material. The at least one sparse representation is produced by the module, referred to below, from the crystal unit cell structure. The crystal unit cell structure has at least one defect. In an embodiment, one sparse representation is produced from an ideal unit cell.

Output Graph:

In the output graph, the global state comprises the model predictions of the target variables. A message-passing layer represents a mapping from G=(V, E, u) to G'=(V',E', u'). Said mapping is based on update rules for at least one of the following: Nodes, edges, and global state. Edge update rule operates on the information from one or more of the following:

A sender $v^s_k$, at least two receiver nodes $v^r_k$, the edge $e_k$, and the global state u.

The update rule is expressed by the following function de:

$$e'_k = \phi_e(v^s_i, v^r_i, e_k, u).|$$

A node update rule aggregates the information received from all the edges $Ev_i=\{e'_k | e'_k \in \text{neighbors}(v_i)\}$ connected to one or more of the following:

The node $v_i$, the node itself $v_i$ and the global state u.

The node update rule is expressed by the following function $\phi_v$:

$$\bar{e}_i = \frac{1}{|E_{v_i}|} \sum_{neighbors(v_i)} e'_k$$

$$v'_i = \phi_v(\bar{e}_i, v_i, u)$$

In an embodiment, the global state "u" is updated based both on the aggregation of both nodes and edges alongside the global state itself.

The aggregation of both nodes and edges is processed with $\phi_u$:

$$\bar{u}_v = \frac{1}{|V|} \sum_{i=0}^{|V|-1} v'_i$$

-continued $$\bar{u}_e = \frac{1}{|E|}\sum_{k=0}^{|E|-1} e'_k$$

$$u' = \phi_u(\bar{u}_v, \bar{u}_e, u)$$

For further explanation of the functions $\phi_v$, $\phi_e$, $\phi_u$:

The functions $\phi_v$, $\phi_e$, $\phi_u$ referred to above represent fully-connected neural networks.

In an embodiment, the model is trained with a so called ordinary backpropagation. In machine learning backpropagation algorithm(s) can be utilized for training feedforward artificial neural networks. Thus, the mean squared error (MSE) loss between the predicted values in the output graph and the target values in the training dataset is minimized.

MEGNet

Other state of the art systems propose so called continuous-filter convolutional layers. In an embodiment, MEGNet-system uses a more advanced GNN. The MEGNet-system uses message-passing instead of convolutional message systems. The MEGNet architecture can be used for predicting the properties of pristine 2D materials.

The MEGNet architecture is also used for choosing the properties of pristine 2D materials that make optimal hosts for engineered point defects. In an embodiment, open source toolkit for materials data mining is used for predicting the properties of structures with point defects.

ReaxFF

The so called ReaxFF-model offers a potential that has been developed for dichalcogenides. The ReaxFF-model may be used for studying defect dynamics. The potential of the ReaxFF-model is computationally efficient. The potential of the ReaxFF-model thus allows to probe dynamics on a larger time scale.

GemNet

Another state of the art system is referred to as GemNet. GemNet redresses an important shortcoming of the previous message-passing GNN's: Loosing of geometric information due to considering only distances as edge features. By way of example, GemNet allows an improved handling of angular information. In an embodiment, a Atomistic Line Graph Neural Network is referred to as ALIGNN.

Dataset Description

In an embodiment, a machine learning friendly 2D material defect database (2DMD) is established for the training purposes. The machine learning friendly 2D material defect database (2DMD) is also established for evaluating of models.

The datasets contain structures with point defects for the most widely used 2D materials.

The 2D material referred to above, is one or more of the following: MoS2, WSe2, hexagonal boron nitride (h-BN), GaSe, InSe, and black phosphorous (BP).

For the point defect types, reference is made to Table 1 below. Table. 1 an example of types of point defects in a set of data. Table 1 has three columns. From left to right, the first column is headed "material". The middle column is headed "substitutions", whereas the right column is headed "vacancies".

The first column lists examples of different elements. The listed elements show point defects in the form of substitutional defects. As an example, the substitutional point defect S→Sc represents the substitution of the S atom by the atom Sc.

In additions, Mo→W shows that the atom Mo has been substituted by the atom W. A vacancy is present at the position of the Mo and S atoms.

Table 1 refers to a machine learning friendly 2D material defect database (2DMD). The datasets of Table 1 contain structures with point defects for the most widely used 2D materials.

The 2D material referred to is one or more of the following: MoS2, WSe2, hexagonal boron nitride (h-BN), GaSe, InSe, and black phosphorous (BP).

TABLE 1

Point defect types present in the dataset

| Material | Substitutions | Vacancies |
|---|---|---|
| $MoS_2$ | S → Se; Mo → W | Mo; S |
| $WSe_2$ | Se → S; W → Mo | W; Se |
| h-BN | B → C; N → C | B; N |
| GaSe | Ga → Se; Se → S | Ga; Se |
| InSe | In → Ga; Se → S | Ga; Se |
| BP | P → N | P |

In an embodiment, the dataset consists of two parts:

The first part refers to a low defect concentration.

In an embodiment, the low defect concentration part comprises 5933 MoS2 structures. The low defect concentration part further comprises 5933 WSe2.

The second part of the dataset comprises a high defect concentration. The second part may also be referred to as a high-density dataset.

The high-density dataset comprises a sample of randomly generated substitution and vacancy defects for all the materials.

All possible configurations in a 8×8 supercell for defect types are depicted in Table 2 (shown below).

In the example, shown in Table 1, the actual supercell size is 8×8. The 4×4 window is centred on the defects to conserve space.

The 2D material referred to above is one or more of the following:

For each total defect concentration 2.5%, 5%, 7.5%, 10%, and 12.5%, a number of 100 structures are generated.

All in all, said 100 structures equal a value of 500 configurations for each material and a number of 3000 in total.

On a whole, in the present example, the dataset comprises 14866 structures with 120-192 atoms each.

DFT Computations

In an embodiment, the so-called density functional theory (DFT) can be utilized. The density functional theory (DFT) uses a PBE functional as implemented in the Vienna Ab Initio Simulation Package (VASP).

In an embodiment, for sampling structures of 2D materials and point defects, sampling is performed by using at least one of the following: An ab initio method on HPC or an open data basis.

An interaction between the valence electrons and ionic cores may be described within a so called projector augmented (PAW) approach. The projector augmented (PAW) approach reveals a plane-wave energy cut-off that takes place at 500 eV.

In the current example, initial crystal structures are obtained from a so called material project database.

In the current example, supercell sizes and the computational parameters for each material are implemented. Supercells of a pre-set size are used for the calculation of defects, Therefore, a so called Brillouin zone was sampled using a so called Γ-point only Monkhorst-Pack grid for structural relaxation.

Also, a denser grid for further electronic structure calculations is employed.

Additionally, a vacuum space of at least 15° A is used to avoid interaction between neighbouring layers.

By way of example, in a structural energy minimization, atomic coordinates are allowed to relax until the forces on all the atoms are less than 0.01 eV/° A.

In this example, an energy tolerance is 10-6 eV.

For defect structures with unpaired electrons, embodiments provide standard collinear spin-polarized calculations with magnetic ions in a high-spin ferromagnetic initialization.

Wherein during ionic and electronic relaxations the ion moments may relax to a low spin state.

Embodiments can be focussed on basic properties of defects at the level of single-particle physics.

In an embodiment, two target variables are used for evaluating machine learning methods:

The first variable refers to a defect formation energy per site. The second variable refers to a so-called HOMO-LUMO gap.

In an embodiment, the formation energy is the energy required to create a defect. The formation energy is defined by the following formula:

$$E_f = E_D - E_{pristine} + \sum_{i \in \{Mo,S\}} n_i\mu_i - \sum_{i \in \{W,Se\}} m_i\mu_i$$

In the above formula:

ED is the total energy of the structure with defects.

E pristine is the total energy of the pristine base material.

$n_i$ is the number of atoms transferred from the supercell to a chemical reservoir.

$m_i$ is the number of atoms transferred from a chemical reservoir to the supercell to form the substitution-type defects.

$\mu_i$ is the chemical potential of i-th element.

To make the results more comparable for examples showing a different number of defects, embodiments normalize the formation energy by dividing it by the number of defect sites.

The corresponding formula is:

$$E'_f = E_f / N_d$$

In the formula Nd represents the number of defects in the structure.

Defects occurring in one or more of the following materials: BP, GaSe, InSe, h-BN have unpaired electrons.

Also, defects occurring in materials referred to above have a non-zero magnetic momentum. In an embodiment, the density functional theory (DFT) is computed, taking into account a spin-up and a spin-down band, resulting in the majority and minority HOMO-LUMO gaps.

For evaluating the machine learning algorithms, embodiments refer to the minimum of those gaps as the target variable.

Predicting Energetic and Electronic Structures of Defects in 2D Materials with Machine Learning As described herein, proposed is a method for predicting the energetic and electronic structures of defects in 2D materials with machine learning.

In a first operation, a machine learning-friendly 2D material defect database is established.

The machine learning-friendly 2D material defect database employs a high throughput density functional theory calculations (DFT).

The density-functional theory (DFT) is a computational quantum mechanical modelling method. The density-functional theory may be used in physics, chemistry and materials science applications. The density-functional theory investigates an electronic structure and/or a nuclear structure of so called many-body systems. A many-body system may be a set of atoms, molecules and/or condensed phases.

The machine learning-friendly 2D material defect database is referred to in the following as a database. The database may comprise both structured datasets and dispersive datasets of defects in represented 2D materials. The datasets are used to evaluate both previously reported and newly developed data.

Sparse Representation of Crystals with Defects

An atomic structure for machine learning algorithms is referred to as a so-called point cloud. The point cloud may be a set of points in a 3D space. Each point of the point cloud is associated with a vector of properties. The vector of properties comprises at least the atomic number.

However, the vector of properties may also comprise at least one physics-based feature. The physics-based feature may be a radius and/or the number of valence electrons. The structures with defects present a challenge to machine learning algorithms.

Embodiments represent structures with defects. The representation of the structures facilitates the prediction of the properties for the ML algorithm.

In an embodiment, the crystal structure is treated as a point cloud of defects. To obtain the point cloud of defects, all atoms that are not affected by at least one defect are removed from the structure with defects. Reference is made to the defects referred to above.

By way of example, virtual atoms are added on the vacancy sites. Embodiments accordingly take the structure with defects, remove all the atoms that are not affected by a defect, and adds virtual atoms on the vacancy sites.

In addition to the coordinates of the point of the point cloud, each point receives two parameters. The first parameter is the atomic number of the atom on the site in the pristine structure. The second parameter is the atomic number of the atom in the structure with the defect. In an embodiment, a vacancy carries the atomic number 0. The structure of the pristine unit cell is encoded as a global state for each structure. Thus, a vector is used with the set of atomic numbers of the pristine material.

Embodiments refer to the point cloud of defects as a set of tuples. Each set of tuples comprising Cartesian coordinates and/or a vector with at least one feature.

Embodiments propose an augmentation that is specific both to the graph neural network (GNN) and to the crystal of the 2D material. The augmentation includes: Adding the difference in the Z-coordinate. The Z-coordinate runs perpendicular to the material surface. The difference in the Z-coordinate may also be referred to as an edge feature. The difference is added in the Z-coordinate, perpendicular to the material surface, as an edge feature. In an embodiment, the feature comprising, adding the difference in Z-coordinate, does not the break a rotational symmetry.

Rather, in the case of a 2D crystal, a direction that is perpendicular to the material surface is physically defined. Being physically defined, the direction that is perpendicular to the material surface and thus may be used.

In a crystal, the replacement of an atom or the introduction of a vacancy causes a disruption of the electronic states.

Given a wave nature of the number of electrons, the introduction of a localized defect creates oscillations in the electronic wave functions at the atomic level. In the case of crystals, the wave function oscillations may involve one or several electronic orbitals.

The amplitude of those oscillations referred to above, decays away from the defect at a rate that depends on the nature of the orbitals. The oscillatory nature of the electronic states, close to a defect, leads to the formation of so called electronic orbital shells (EOS). Electronic orbital shells (EOS) occur where the wave function shows a constant amplitude around the defect.

Embodiments associate to these shells an EOS index. It goes without saying that other indices may also apply in addition to the aforementioned EOS index. Thus, the amplitude of the wave function is labelled in a decreasing order.

Embodiments project all atoms on the x-y plane. The first operation leads to a 2D representation of the 2D material at question. In the case of a binary crystal, for each atom, embodiments draw circles. The circles are centred on the relevant atom. Also, the circles pass through the atoms of the other species. The circles number the atoms of the other species in the order of radius increase. In case of unary materials, the circle radii are multiples of the unit cell size. The circle number is represented by the EOS index of the site with respect to the central atom.

With regard to the aforementioned index, embodiments further state that an interaction strength of the atomic electron shells is not monotonic with respect to the atom distance. Instead it oscillates in a way such that minima and maxima coincide with the crystal lattice nodes. In order to represent the oscillations referred to above, embodiments also add parity of the EOS index. To be recognized as a separate feature of the embodiments, the EOS index may also be called EOS parity.

Incorporating Sparse Representation into a Graph Neural Network (GNN)

In an embodiment, the sparse representation fits into the graph neural networks (GNN) framework as follows:

1. Graph nodes correspond to point defects.

It goes without saying that instead of all, only a number the atoms in a structure are affected by point defects;

2. A threshold that is established for connecting nodes with edges, is increased;
3. Node attributes comprise the atomic number of the atom on the site in the pristine structure. Said node attributes also comprise the atomic number of the atom in the structure with defect. With "0" representing a vacancy.
4. Edge attributes comprise the Euclidean distance between point defects corresponding to the adjacent vertices. The edge attributes also comprise an EOS index and/or an EOS parity index and/or the Z plane distance.
5. The input global state comprises the chemical composition of the crystal as a vector of atomic numbers.

Physics-Based Descriptors

Another embodiment reveals that the crystal unit cell structure is obtained, using at least one physically motivated descriptor and/or an embedding machine learning model. To show a comparison between a classic setup and graph neural networks (GNN) embodiments also evaluate a classic setup. In the classic setup physics-based descriptors are combined with a classic machine learning algorithm for tabular data.

Embodiments extract the numerical features from the crystal structures using the mat miner package.

Reference is made to Table 2 below.

TABLE 2

| Features | Description |
|---|---|
| Density | Structure density, volume per atom, maximum packing fraction and maximum packing efficiency |
| Structural Complexity [34] | Shannon information entropy of a structure |
| XRD Powder Pattern [35] | Powder diffraction of a structure |
| Orbital Field Matrix [36] | Representation based on the valence shell electrons of neighboring atoms |
| JarvisCFID [37] | Pairwise radial, nearest neighbor, bond-angle, dihedral-angle and core-charge distributions |

Table 2 shows so-called mat miner feature groups used for a defect configuration description. According to another embodiment of the invention the crystal unit cell structure is obtained, using at least one physics based descriptor and/or an embedding machine learning model.

A complete comparison is achieved by evaluating a classic setup, where physics-based descriptors are combined with a classic machine learning algorithm for tabular data, CatBoost.

The numerical features are extracted from the crystal structures using the mat miner package as outlined in Table 2.

Evaluation Scheme

Aggregate Performance

By way of example, embodiments split the dataset into 3 parts, shown below: train (60%), validation (20%), and test (20%).

Embodiments stratifies the split with the respect to each base material, respectively.

A random search for hyper parameter optimization is used for each model:

The random search comprises the following operations:

A number of 50 hyper parameter configurations are generated.

The model is trained with each configuration on the train part.

A selection is made to obtain the best performing configuration in each case. For this purpose, the quality of the validation part is evaluated.

The final result is obtained by training each model with the optimal parameters on the combination of train and validation parts.

The quality is evaluated on the un-seen test part.

The test is repeated over a predetermined number of test runs.

By way of example, to estimate the effects of the random initialization, 12 test runs are assumed in the following.

Embodiments use unrelaxed structures as inputs.

After completion of a relaxation period, embodiments predict the energy and the HOMO-LUMO gap.

To perform the prediction, embodiments use a weighted mean absolute error (MAE) as the quality metric:

$$MAE = \frac{\sum_{i=1}^{N} |\bar{y}_i - y_i| w_i}{\sum_{i=1}^{N} w_i},$$

In the formula shown above:

$w_i$ is the weight assigned to each example.

$y_i$ is the predicted value.

$\bar{y}_i$ is the true value.

N is the number of the structures in the dataset.

In an embodiment, the purpose of using weights is to prevent the combined error value from being dominated by the low defect density dataset part.

By way of example, the low defect density dataset part is 4 times more numerous compared to the high defect density part.

Also as an example, it is assumed that the weights are computed as follows:

$$w_{part} = \frac{N_{total}}{C_{parts} N_{part}}$$

In the formula shown above:

The W dataset is the weight associated with each example in a dataset part.

N total=14866 is the total number of examples.

C parts=8 is the total number of dataset parts. With 2 representing the "low-density", and "6" representing high-density.

N part={500, 5933} represents the number of examples in the part. A value of 500 is assumed for low defect density parts. Wherein a value of 5933 is assumed for the high defect density parts.

Quantum Oscillations Prediction

Embodiments evaluate the models referred to above with respect to learning quantum oscillations. Embodiments use the following test dataset:

MoS2 with one Mo, and one S vacancy.

The residual 2DMD dataset is used as the training dataset.

No sample weighting is used by embodiments.

The training of every model is repeated over a predetermined number of training runs. By way of example, embodiments train every model 12 times with optimal hyper parameters, found via random search.

Embodiments further train every model 12 times with default parameters.

Results

Aggregate Performance

Embodiments compares the performance of the sparse representation combined with MEGNet to one or more of the following so called baseline methods: MEGNet, SchNet, and GemNet.

The baseline methods work on the basis of full representation and so called CatBoost with mat miner-generated features. The results are presented in Table 3 below. Table 3 shows the performance of the different methods in terms of the mean absolute error (MAE). In an embodiment sparse is the representation implemented in the MEGNet model with all the improvements enabled.

SchNet, GemNet, MEGNet have full structures as their input has no additional features.

All the models are trained on the same dataset, comprising stratified samples of all the parts of the 2DMD dataset.

The term "combined" in Table 3 refers to the whole test sample, with the error contributions weighted. The individual material/density combinations refer to the subsets of the combined test dataset.

The term "error" indicates the standard deviation of the results obtained from 12 experiments with the same datasets and model parameters, but different random initialization.

TABLE 3

Formation energy per site MAE; meV; lower is better

| Material | Density | SchNet | GemNet | MEGNet (Fall) | CatBoost | Sparse (MEGNet) |
|---|---|---|---|---|---|---|
| combined | both | 631 ± 31 | 483 ± 91 | 158 ± 47 | 164 ± 5 | 43 ± 5 |
| BP | high | 2088 ± 72 | 1490 ± 429 | 198 ± 211 | 382 ± 30 | 80 ± 10 |
| GaSe | high | 245 ± 12 | 230 ± 41 | 107 ± 25 | 103 ± 4 | 48 ± 7 |
| InSe | high | 268 ± 19 | 247 ± 26 | 95 ± 27 | 137 ± 5 | 35 ± 2 |
| MoS2 | high | 321 ± 100 | 235 ± 206 | 136 ± 22 | 136 ± 5 | 23 ± 5 |
| WSe2 | high | 536 ± 123 | 575 ± 181 | 112 ± 33 | 162 ± 6 | 23 ± 4 |
| h-BN | high | 1442 ± 68 | 697 ± 315 | 496 ± 229 | 363 ± 17 | 127 ± 16 |
| MoS2 | low | 65 ± 5 | 44 ± 14 | 358 ± 11 | 12.6 ± 0.4 | 4 ± 1 |
| WSe2 | low | 85 ± 22 | 42 ± 9 | 65 ± 16 | 16.3 ± 0.8 | 6 ± 1 |

HOMO-LUMO gap MAE, meV; lower is better

| Material | Density | SchNet | GemNet | MEGNet (Fall) | CatBoost | Sparse (MEGNet) |
|---|---|---|---|---|---|---|
| combined | both | 224 ± 111 | 166 ± 42 | 112 ± 3 | 117 ± 1 | 112 ± 3 |
| BP | high | 208 ± 20 | 176 ±10 | 170 ± 4 | 174 ± 2 | 187 ± 9 |
| GaSe | high | 309 ± 83 | 196 ± 11 | 178 ± 8 | 173 ± 4 | 194 ± 11 |
| InSe | high | 214 ± 69 | 178 ± 22 | 156 ± 7 | 155 ± 1 | 167 ± 15 |
| MoS2 | high | 204 ± 121 | 174 ± 111 | 54 ± 4 | 71 ± 4 | 39 ± 4 |
| WSe2 | high | 186 ± 177 | 268 ± 182 | 47 ± 3 | 106 ± 6 | 38 ± 4 |
| h-BN | high | 244 ± 24 | 227 ± 6 | 233 ± 4 | 208 ± 3 | 260 ± 14 |
| MoS2 | low | 187 ± 180 | 46 ± 42 | 30 ± 2 | 26.7 ± 0.8 | 5.7 ± 0.2 |
| WSe2 | low | 286 ± 224 | 64 ± 46 | 32 ± 5 | 18.3 ± 0.6 | 8.1 ± 0.6 |

By way of example, for an energy prediction, the model used by embodiments achieves 3.7× less combined MAE, compared to the best baseline model. With the best baseline model achieving a 2.2×-6.0× difference in individual dataset parts.

The example embodiments show a prediction quality for MoS2 and WSe2 improved by a factor of 1.3-4.8. The improvement is outweighted however, by a factor of 1.06-1.15 increase in MAE for the other materials. MAEs results are averaged over the absolute error values.

Following an example performed by embodiments, in terms of computation time, being trained on a Tesla V100 GPU, a MegNet module with sparse representation took 45 minutes; A MegNet module with full representation took 105 minutes. In the example, the GemNet-module took 210 minutes. SchNet took 100 minutes, whereas CatBoost needed 0.5 minutes.

In an embodiment, both a low memory footprint and GPU utilization allow to fit 4 simultaneous runs with sparse representation on the same GPU (16 GiB RAM).

Contrary to GNNs running on full representation, this has been done, without losing speed.

Quantum Oscillation

Table 3 shows the performance of the sparse representation in combination with low-density data.

Figure 3:
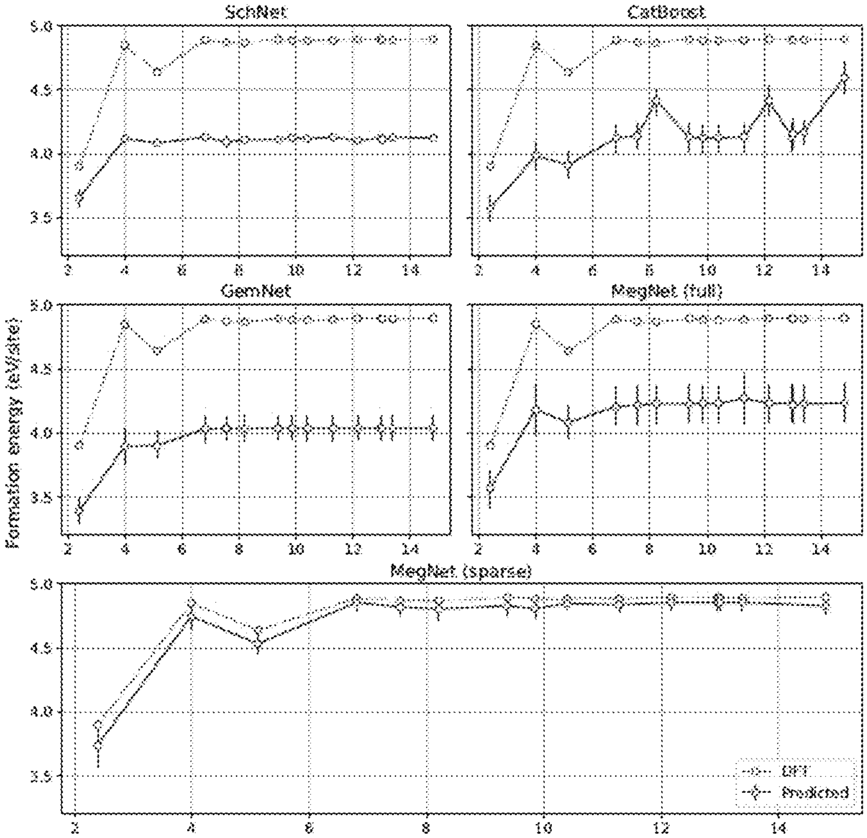
FIG. 3 depicts a predicted and DFT formation energy as a function of the distance between defects, according to an embodiment.

As shown in FIG. 3, the behaviour achieved by embodiments may extend to 2-vacancy data. Accordingly, baseline modules fail to meaningfully learn the required dependencies.

Sparse representation as used by embodiments succeed in doing so. Sparse representation learns the required dependencies including the non-monotonous reduction at 5° A.

Ablation Study

In an embodiment, an ablation study shows how much each proposed improvement contributes to the final result.

A related example is shown in Table 4 below. Table 4 shows the performance of various combinations of the features described herein.

The term "Full" means: The full structure is used as a MEGNet input. The term "Sparse" means: The sparse structure is used as MEGNet input. The term "Sparse-Z" means: Sparse-Z adds the Z coordinate differences in edges. The term "Sparse-Z-Were" means: Sparse-Z-Were adds the atomic species of the pristine material on the defects site as a node feature. The term "Sparse-Z-Were-EOS" means: Sparse-Z-Were-EOS add the EOS index and the EOS parity as edge features.

Following Table 4, the importance of the pristine species for h-BN lies in that both atoms can be substituted to C. The Table 4 is based on the fact that without the additional information, a distinction between B and N substitutions performed by the model is not feasible. Table 4 expresses that adding EOS improves both an expected prediction quality and a prediction stability by a small amount for the low-density datasets.

As far as the HOMO-LUMO gap is concerned, Sparse-Z-Were and Sparse-Z-Were-EOS perform similarly to Full in terms of the combined metric. Referring to the HOMO-LUMO gaps, Sparse-Z-Were and Sparse-Z-Were-EOS outperform it by a factor of 4 for low-density data. EOS again improves prediction quality and stability by a small amount for the low-density datasets.

To conduct the ablation study, embodiments adopt optimal configurations for MEGNet with sparse and full representations found by random search.

The resulting models are trained and evaluated. Experiments are performed over a predetermined number of test runs. By way of example, embodiments use a value averaged over 12 experiments to estimate a training stability. For formation, the energy enabling the Z coordinate difference in sparse representation edges allows the Sparse-Z model to outperform the Full model everywhere except h-BN. Thereby adding pristine atom species (Sparse-Z-Were) as the node features contribute the most of the remaining gain.

TABLE 4

| Formation energy per site MAE; meV; lower is better | | | | | | |
|---|---|---|---|---|---|---|
| Material | Density | Full | Sparse | Sparse-Z | Sparse-Z-Were | Sparse-Z-Were-EOS |
| combined | both | 158 ± 47 | 432 ± 29 | 104 ± 24 | 42 ± 4 | 43 ± 5 |
| BP | high | 198 ± 211 | 116 ± 18 | 104 ± 16 | 75 ± 9 | 80 ± 10 |
| GaSe | high | 107 ± 25 | 76 ± 9 | 66 ± 10 | 48 ± 7 | 48 ± 7 |
| InSe | high | 95 ± 27 | 81 ± 8 | 69 ± 8 | 34 ± 3 | 35 ± 2 |
| MoS2 | high | 136 ± 22 | 223 ± 21 | 96 ± 15 | 23 ± 4 | 23 ± 5 |
| WSe2 | high | 112 ± 33 | 147 ± 27 | 63 ± 11 | 23 ± 2 | 23 ± 4 |
| h-BN | high | 496 ± 229 | 2741 ± 202 | 2792 ± 184 | 123 ± 14 | 127 ± 16 |
| MoS2 | low | 58 ± 11 | 37 ± 15 | 19 ± 4 | 5 ± 2 | 4 ± 1 |
| WSe2 | low | 65 ± 16 | 30 ± 9 | 21 ± 5 | 7 ± 2 | 6 ± 1 |

| HOMO-LUMO gap MAE, meV; lower is better | | | | | | |
|---|---|---|---|---|---|---|
| Material | Density | Full | Sparse | Sparse-Z | Sparse-Z-Were | Sparse-Z-Were-EOS |
| combined | both | 112 ± 3 | 148 ± 5 | 121 ± 2 | 114 ± 7 | 112 ± 3 |
| BP | high | 170 ± 4 | 197 ± 10 | 192 ± 9 | 188 ± 18 | 187 ± 9 |
| GaSe | high | 178 ± 8 | 237 ± 12 | 205 ± 16 | 207 ± 16 | 194 ± 11 |
| InSe | high | 156 ± 7 | 170 ± 8 | 172 ± 14 | 160 ± 9 | 167 ± 15 |
| MoS2 | high | 54 ± 4 | 110 ± 10 | 45 ± 2 | 40 ± 5 | 39 ± 4 |
| WSe2 | high | 47 ± 3 | 173 ± 13 | 66 ± 4 | 39 ± 6 | 38 ± 4 |
| h-BN | high | 233 ± 4 | 265 ± 16 | 271 ± 11 | 267 ± 21 | 260 ± 14 |
| MoS2 | low | 30 ± 2 | 12 ± 1 | 7.2 ± 0.4 | 6.0 ± 0.7 | 5.7 ± 0.2 |
| WSe2 | low | 32 ± 5 | 19 ± 1 | 11.7 ± 0.6 | 8.4 ± 0.6 | 8.1 ± 0.6 |

Performance of various combinations of our proposed features, Full—full structure is used as MEGNet Sparse—sparse structure use as MEGNet input; Sparse-Z add z coordinate differences in edges; Sparse-Z-Were adds the atomic species of the pristine material on the defects site as a node feature; Sparse-Z-Were-EOS add EOS index and EOS parity as edge features.

Advantages of the Described Embodiments

A variety of properties may be obtained via controlled defect introduction.

The need for the crystals referred to above, is huge. Corresponding ab initio calculations are extremely expensive. Therefore, it is important to have a way to predict the properties of a crystal with a certain defect configuration.

Embodiments propose a machine learning approach for rapidly estimating 2D material properties. The proposed machine learning approach assumes both a given lattice structure and a defect configuration.

The method proposes a way to represent a 2D material configuration that allows a neural network to train quickly and accurately.

The method proves to be far less error-prone than known systems.

As far as training and inference is concerned, embodiments prove to be more resource efficient.

Embodiments provide a significant increase in prediction accuracy compared to the state-of-the-art general methods.

A high accuracy allows to reproduce the nonlinear non-monotonic property-distance correlation of defects which is a combination of the quantum mechanics effect and the periodic lattice nature in 2D materials.

Embodiments also shows great transferability for a wide range of defect concentrations in a variety of 2D materials.

Instead of treating a crystal structure as a point cloud of atoms, embodiments refer to a point cloud of defects.

Embodiments focus on the prediction of the properties of crystals blended with defects, substitutions, and/or vacancies.

Embodiments propose the use of a sparse representation combined with graph neural network architectures like MEGnet.

It is the intention to show that embodiments dramatically improve an energy prediction quality.

Studies following embodiments demonstrate that a prediction error drops 3.7 times compared to the nearest state of the art module.

The representation of embodiments is compatible with any machine learning algorithm based on point clouds.

Computationally, the training of a graph neural network (GNN) using sparse representation takes at least 4× less memory and/or 8× less GPU operations compared to the full representation.

Embodiments give both a practical and a sound way to explore a vast domain of possible crystal configurations confidently.

FIG. 1*a* to FIG. 1*d* show the transition from a full representation (FIG. 1*a*) to a sparse representation (FIG. 1*d*) using the example of a MoS2 supercell.

Below each FIG. 1*a* to 1*d* an explanation of the symbols "W", "Mo", "Se", "S" and "S Vacancy" is shown.

FIG. 1*a* shows a full MoS2 structure with one Mo→W substitution and two S→Se substitutions.

Also, there are two S vacancies.

Figure 1B:
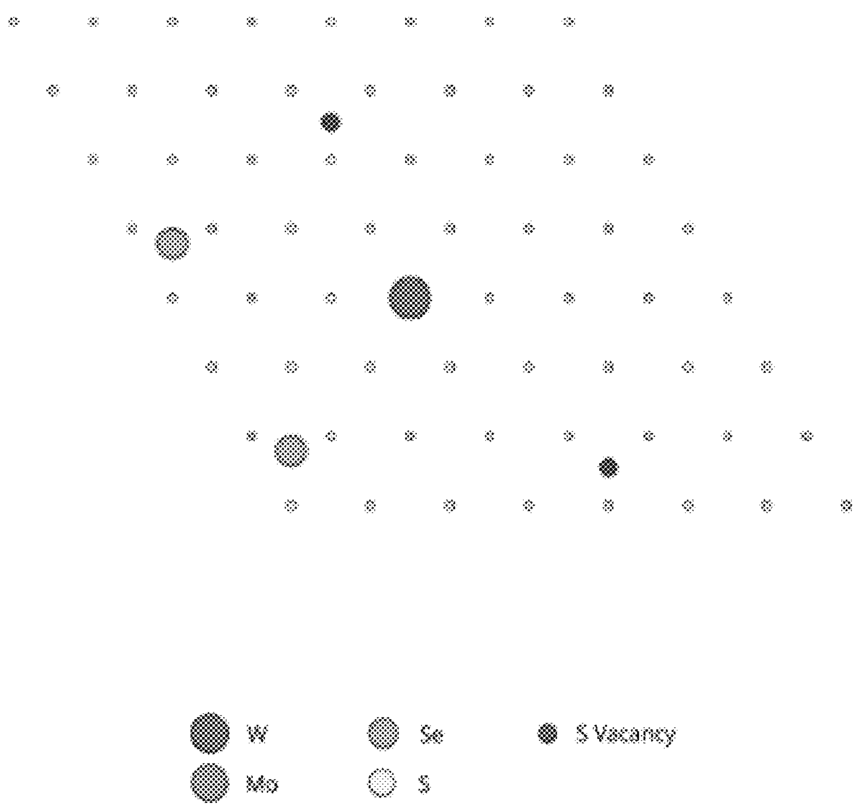

FIG. 1*b* shows a sparse representation. The sparse representation of FIG. 1*b* comprises only defect types and coordinates.

Figure 1C:
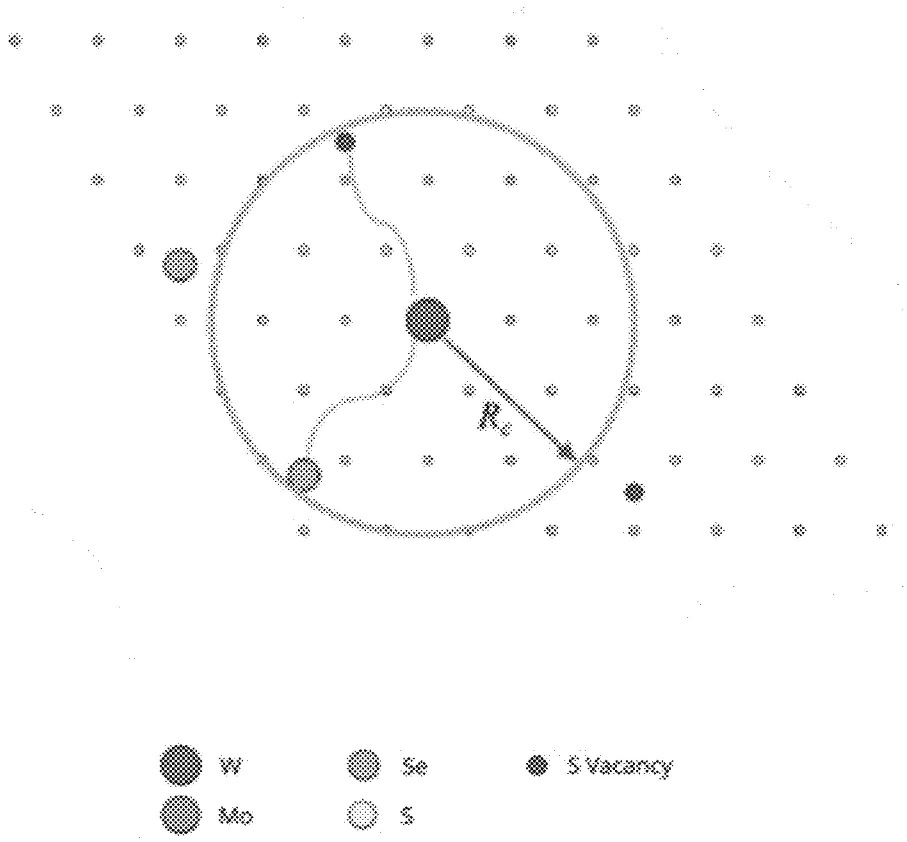

FIG. 1*c* represents the intermediate point of the graph construction.

The cut off radius is centred on the metal substitution defect.

Figure 1D:
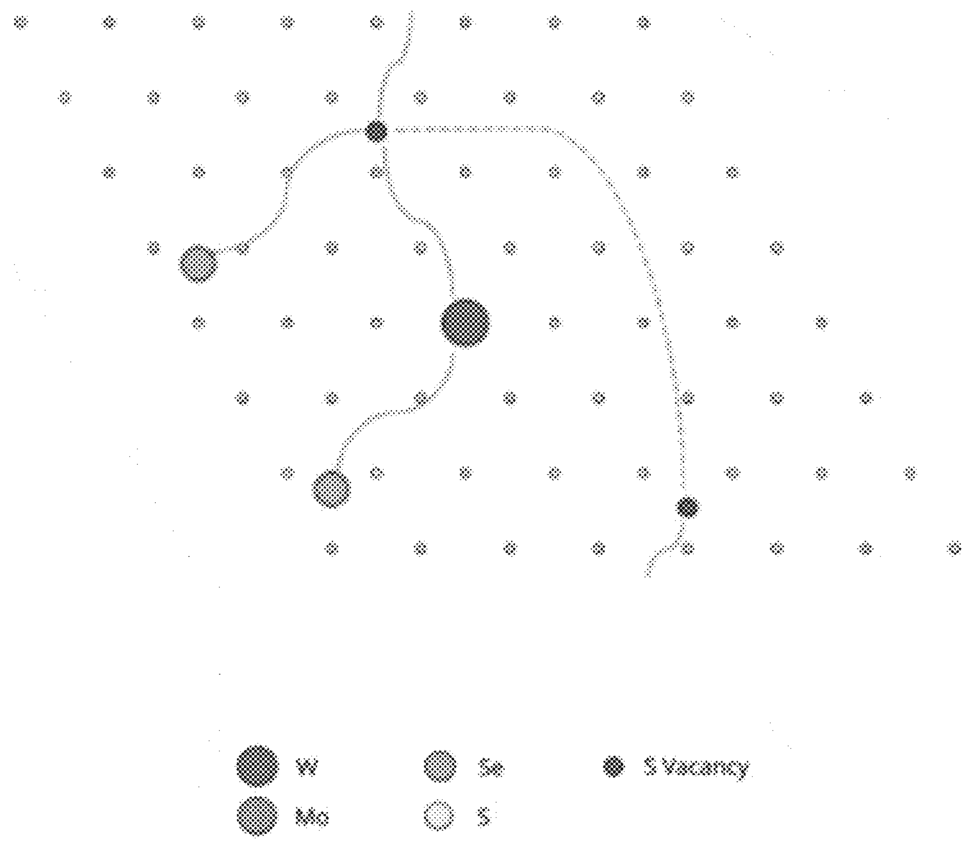

FIG. 1*d* shows the final graph with the sparse representation.

A dashed green line shown in FIG. 1*d* indicates a virtual graph edge that effectively connects one node with another via a periodic boundary condition.

Figure 2:
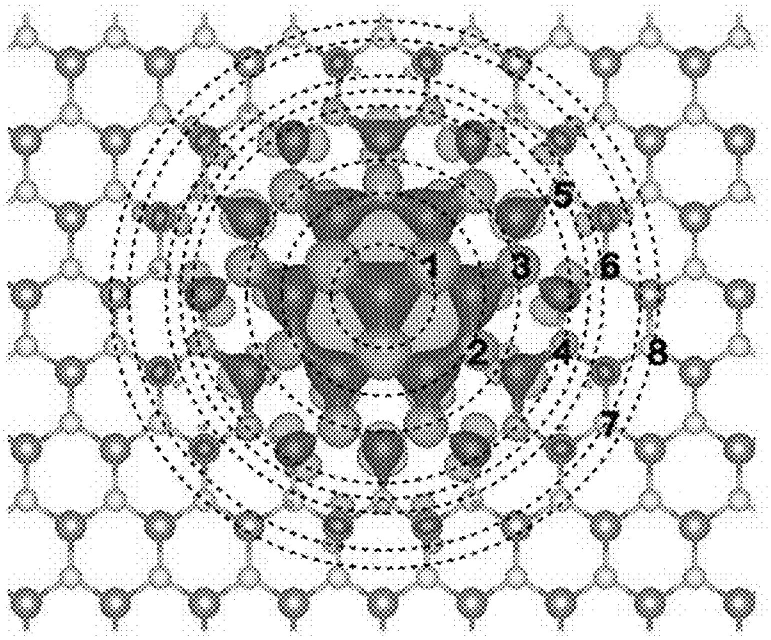
FIG. 2 is an electronic orbital shell illustration centred at an Mo atom of a MoS2 crystal lattice, according to an embodiment.

FIG. 2 shows an illustration of electronic orbital shells.

The orbital shells are centred at an Mo atom of a MoS2 crystal lattice.

The red and green colours represent the opposite phases of an isosurface of a defect wave function simulated by DFT.

The isosurface is a three-dimensional analogy of an isoline. The isosurface is a surface that represents points of a constant value within a volume of spaces.

FIG. 3 shows a predicted and DFT formation energy as a function of the distance between the defects for MoS2 with one Mo and one S vacancy.

As shown in Table 3, sparse representation performs especially well on the low-density data.

This behaviour of the sparse representation extends to the 2-vacancy data, as shown in FIG. 3.

Figure 4:
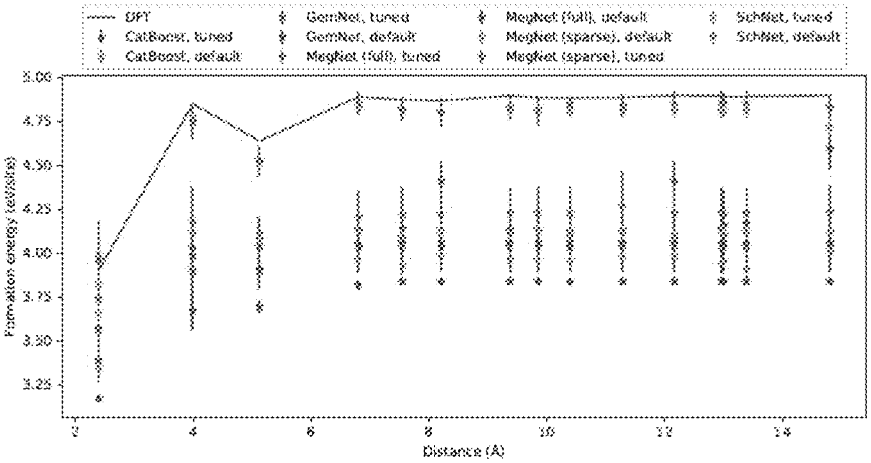
FIG. 4 depicts a predicted and DFT formation energy as a function of the distance between the defects for MoS2 with one Mo and one S vacancy, according to an embodiment.

FIG. 4 represents a predicted and DFT formation energy as a function of the distance between the defects for MoS2 with one Mo and one S vacancy.

Additionally to FIG. 3, the FIG. 4 applies to models with both tuned and default hyper parameter values.

The results for the quantum oscillation experiment with the default hyper parameter values are shown in FIG. 3.

The results for the quantum oscillation experiment with both default and tuned in values are shown in FIG. 4.

FIG. 4 addresses the concern that 80% of MoS2 dataset is used for hyper parameter tuning.

Figure 5:
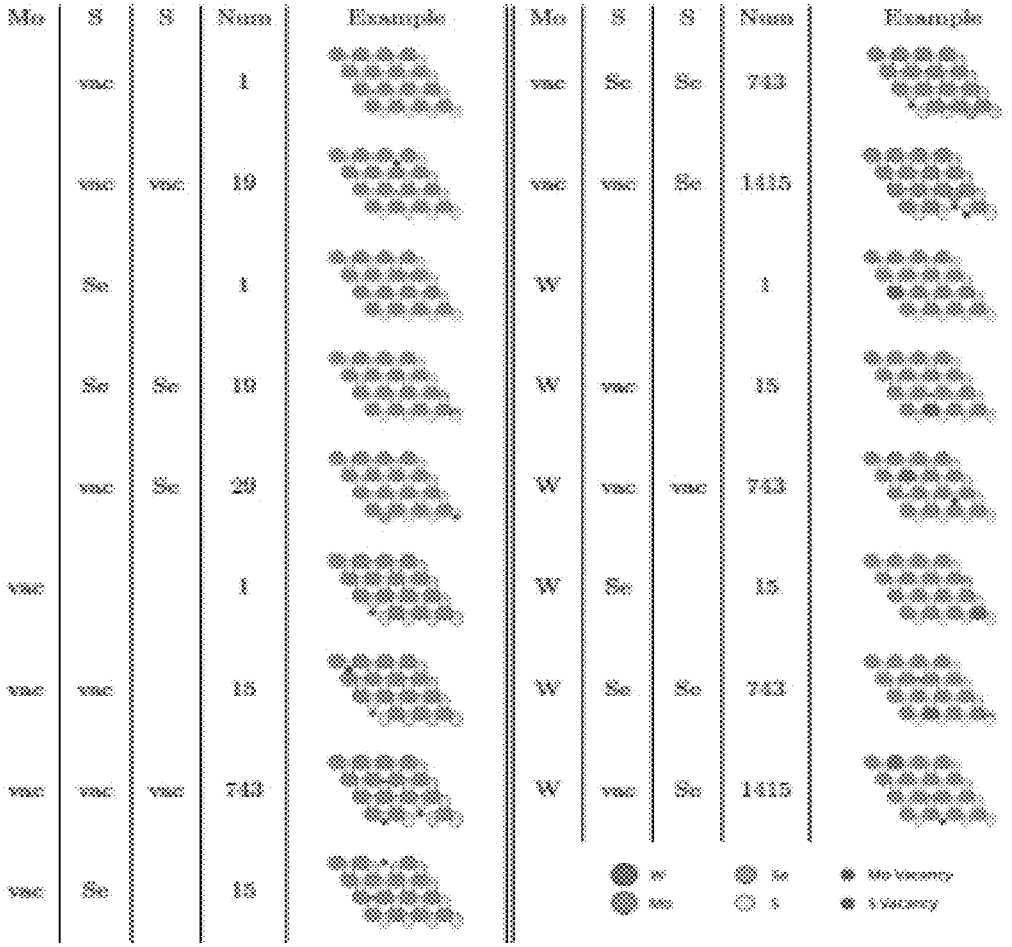
FIG. 5 depicts a variety of defect types in a low density dataset, according to an embodiment.

Referring to FIG. 5, defect types in a low density dataset are depicted, according to an embodiment. The "Mo" and two "S" columns denote the type of site that is being perturbed either by substituting the listed element, or a vacancy (vac). "Num" column includes the number of structures with defects of the type in the dataset. Finally, "Example" column presents a structure with such a defect. Note that the actual supercell size is 8×8, and depicted herein is a 4×4 window centred on the defects for ease of illustration.

The invention claimed is:

1. A method for predicting at least one property of a crystal of a material, wherein the crystal exhibits at least one point defect, using at least one module for sampling structures of materials and the at least one point defect of the crystal, the method comprising:
- sampling structures of materials and point defects using the at least one module;
- providing a neural network, wherein with the neural network:
  - receiving as inputs:
    - a structure of the material as one of the sampled structures of materials and which is represented by a cloud of defect points, and
    - an ideal crystal unit cell structure represented by a global state vector, and
  - outputting at least one predicted property of the crystal as a vector using a generated set of data,
  - wherein within the neural network, the at least one point defect is defined according to: a set of coordinates, a type of point defect, and a crystal unit cell structure.

2. The method of claim 1, wherein materials of the crystal are 2D materials, and an input structure of the material is sparse.

3. The method of claim 2, wherein the 2D material is a transition metal dichalcogenide, a boron nitride, or a graphene.

4. The method of claim 1, wherein the at least one point defect is represented as a tuple, with the tuple comprising a first component and a second component, wherein the first component comprises a set of coordinates and a type of point defect, and the second component comprises a crystal unit cell structure represented as a vector.

5. The method of claim 1, wherein the module creates a sparse representation from the crystal unit cell structure, wherein the crystal unit cell structure includes at least one of:

at least one defect, and produces one sparse representation from an ideal unit cell.

6. The method of claim 1, wherein the crystal unit cell structure is described using at least one of: one physically motivated descriptor and an embedding machine learning model.

7. The method of claim 1, wherein the at least one predicted property of the crystal includes at least one of electronic properties, optical properties, mechanical properties, or thermal properties.

8. The method of claim 1, wherein the neural network is trained on a set of data including a plurality of 2D materials and point defects.

9. The method of claim 1, wherein the cloud of defect points is represented as a tuple, the tuple comprising a set of coordinates and a type of defect point.

10. The method of claim 1, wherein the global state vector includes information related to the crystal unit cell structure and the at least one point defect.

11. A non-transitory computer-readable medium comprising:

instructions for performing a method for predicting at least one property of a crystal of a material, wherein the crystal exhibits at least one point defect, the instructions including:

sampling structures of materials and point defects;

providing a neural network, wherein with the neural network:

receiving as inputs:

a structure of the material as one of the sampled structures of materials and which is represented by a cloud of defect points, and an ideal crystal unit cell structure represented by a global state vector, and outputting at least one predicted property of the crystal using a generated set of data, wherein within the neural network, the at least one point defect is defined according to:

a set of coordinates, a type of point defect, and a crystal unit cell structure.

12. A system for predicting at least one property of a crystal of a material exhibiting at least one point defect, the system comprising:

a module for sampling structures of materials and the at least one point defect, a neural network for predicting the at least one property, and a processor for executing instructions including:

sampling structures of materials and point defects;

providing a neural network, wherein with the neural network:

receiving as inputs:

a structure of the material as one of the sampled structures of materials and which is represented by a cloud of defect points, and an ideal crystal unit cell structure represented by a global state vector, and outputting at least one predicted property of the crystal using a generated set of data;

wherein within the neural network, the at least one point defect is defined according to: a set of coordinates and a type of point defect, and a crystal unit cell structure.

13. The system of claim 12, wherein materials of the crystal are 2D materials, and an input structure of the material is sparse.

14. The system of claim 13, wherein the 2D material is a transition metal dichalcogenide, a boron nitride, or a graphene.

15. The system of claim 12, wherein the module creates a sparse representation from the crystal unit cell structure, wherein the crystal unit cell structure includes at least one of:

at least one defect, and produces one sparse representation from an ideal unit cell.

16. The system of claim 12, wherein the crystal unit cell structure is described using at least one of:

one physically motivated descriptor and an embedding machine learning model.

17. The system of claim 12, wherein the at least one predicted property of the crystal includes at least one of electronic properties, optical properties, mechanical properties, or thermal properties.

18. The system of claim 12, wherein the neural network is trained on a set of data including a plurality of 2D materials and point defects.

19. The system of claim 12, wherein the cloud of defect points is represented as a tuple, the tuple comprising a set of coordinates and a type of defect point.

20. The system of claim 12, wherein the global state vector includes information related to the crystal unit cell structure and the at least one point defect.

* * * * *